United States Patent [19]
Marchand et al.

[11] Patent Number: 5,562,591
[45] Date of Patent: Oct. 8, 1996

[54] RECEPTACLE WITH A TRANSPORT CASE IN A PIPE

[75] Inventors: Robert Marchand, Equeurdreville; Michel Herbreteau, Cherbourg; Joseph Besnier, Acqueville, all of France

[73] Assignee: Compagnie Generale Des Matieres Nucleaires, Velizy-Villacoublay, France

[21] Appl. No.: 302,581

[22] Filed: Sep. 7, 1994

[30] Foreign Application Priority Data

Sep. 14, 1993 [FR] France .................................... 93 10916

[51] Int. Cl.⁶ ..................................................... A62D 3/00
[52] U.S. Cl. ........................... 588/259; 215/247; 406/190; 588/249
[58] Field of Search ..................................... 588/249, 259; 215/247, 249; 406/187–190; 604/244

[56] References Cited

U.S. PATENT DOCUMENTS

| | | | |
|---|---|---|---|
| 2,459,304 | 1/1949 | Blank | 215/247 |
| 2,494,456 | 1/1950 | Still . | |
| 3,072,362 | 1/1963 | Allen | 406/188 |
| 3,266,751 | 8/1966 | Purdy et al. | 406/189 |
| 3,603,471 | 9/1971 | Harris et al. | 604/244 X |
| 3,612,438 | 10/1971 | Herndon | 406/190 |
| 3,667,702 | 6/1972 | Kelley | 406/190 |
| 4,324,511 | 4/1982 | Irish | 406/190 X |
| 4,582,207 | 4/1986 | Howard et al. | 215/247 |

FOREIGN PATENT DOCUMENTS

| | | |
|---|---|---|
| 0093609 | 11/1983 | European Pat. Off. . |
| 1401233 | 4/1965 | France . |
| 80/00371 | 3/1980 | WIPO . |

*Primary Examiner*—Dennis L. Taylor
*Attorney, Agent, or Firm*—Pearne, Gordon, McCoy & Granger

[57] ABSTRACT

A receptacle (59) is provided which includes a flask (22) surrounded by a casing (23) able to slide into a pipe by pneumatic means. A composite element (33, 40) formed of all of one piece is used to close both the openings of the flask and casing by means of screwing. These improvements and others render the receptacle extremely suitable for a large number of measurements carried out in shielded analysis boxes for dangerous samples, especially radioactive ones.

10 Claims, 3 Drawing Sheets

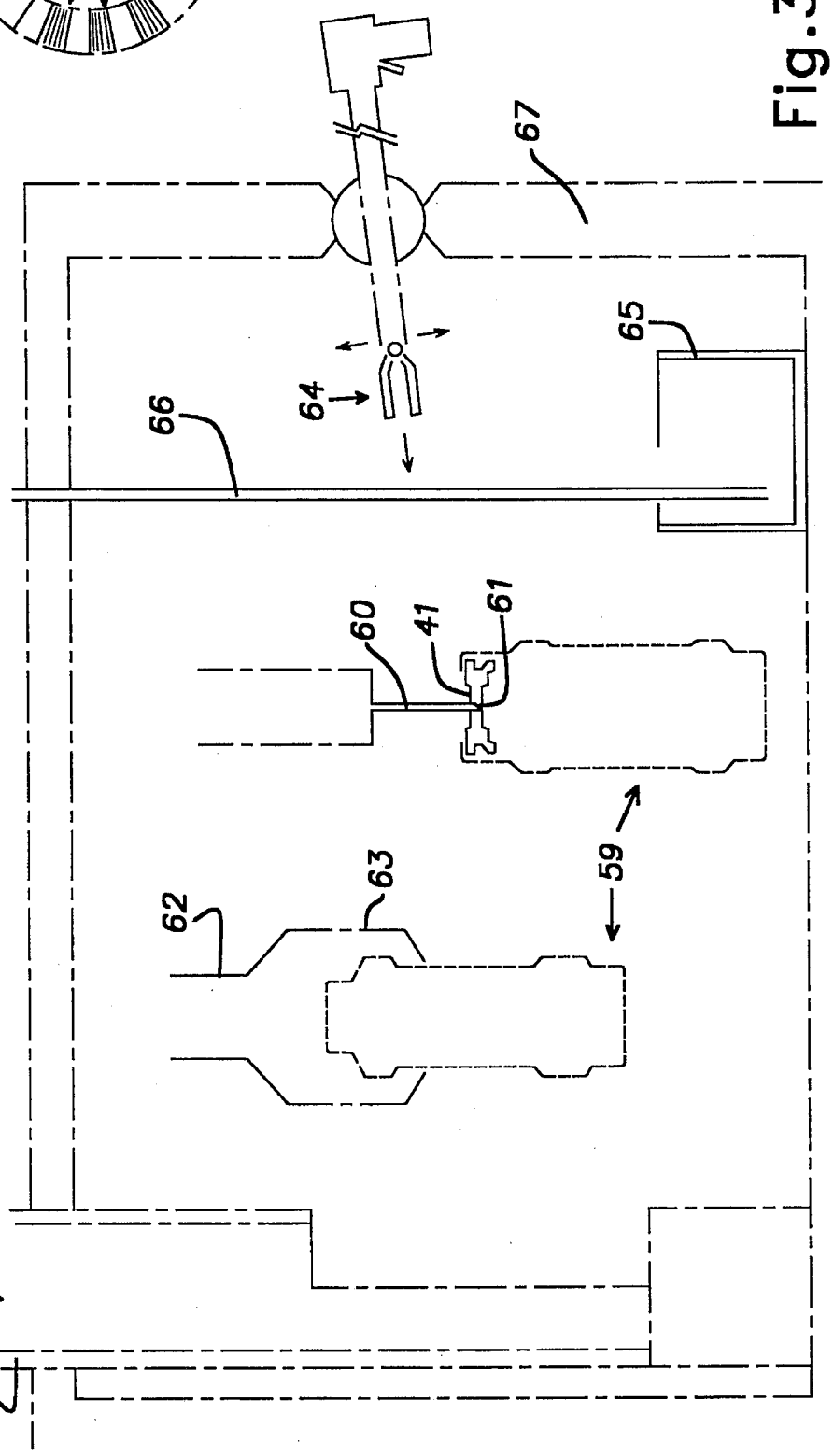

RECEPTACLE WITH A TRANSPORT CASE IN A PIPE

FIELD OF THE INVENTION

The invention concerns a receptacle with a flask and a transport casing and is moved in a pipe.

BACKGROUND OF THE INVENTION

The receptacles in this document are more particularly those intended to contain dangerous substances, such as radioactive ones, to be carried by pneumatic means in pipes between product filling, sampling, analysis and reject stations making up the measurement installation. As regards the prior art, the receptacle shown on FIG. 1 includes a small jug 1 which, is intended to contain a product to be analysed, and a cursor 2 which surrounds the small jug 1. The small jug 1 is closed by a stopper 3 and the cursor 2, which like the small jug has an opening, is closed by a cap 4. The small jug 1 is housed with a large amount of play in the cursor 2. The cursor 2 is fitted with two annular flanges 5 and 6 enabling it to easily slide in pneumatic pipes. The flexible elastomer stopper 3 is composed of a circular internal lip 7 moulded onto the opening wall of the small jug 1 with a flat pricking surface 8 and intended to be pierced by needles for filling the small jug 1 and taking samples from the small jug 1, and a skirt 9 folded back around the opening edge of the small jug 1 in the position shown where the small jug 1 and cursor 2 are closed. The lower lip 7 is provided at its end with a swelling 10 which makes it possible to retain against the pricking surface 8 a drop catcher 11 composed of a ring 12 mounted in the internal lip 7 and a valve 13 parallel to the pricking surface 8 and whose rôle, as its name indicates, is to wipe dry the needles extracted from the small jug 1, thus retaining the liquid drop which could be suspended from it. Before being folded back, the skirt 9 significantly extends the internal lip 7 opposite the pricking surface 8.

The cursor 2 is provided with a hole 14 in front of the pricking surface 8 so as to allow the needles to reach the small jug 1. As for the cap 4, this is made of flexible plastic and locked by virtue of an internal edge 15 at its end on an external swelling 16 of the opening of the cursor 2.

This conception is subject to a large number of drawbacks which considerably reduce its advantages. In particular, it is necessary to carry out samplings by means of needles as it is impossible to temporarily open the small jug 1 by removing the stopper 3 : the dangerous nature of the substances carried means that the small jugs be remote-handled and the only tools available in the existing installation are pliers able to remove the stopper 3 but not replace it as the skirt 9, which remains folded back, opposes any new driving in of the stopper 3 by rubbing against the edge of the small jug 1 and is too flexible so as to be able to straighten it.

The contaminating liquid droplets, which may appear despite the drop catcher 11 when the needle comes out of the pricking surface 8, flow firstly between the small jug 1 and the cursor 2 and permanently pollute them, and secondly remain on this pricking surface 8 with the result on account of the movements transmitted to the small jug/cursor unit to also pollute the sampling installation, the pipes of the pneumatic network and the station of the installation where the small jugs 1 have left the cursors 2 so as to be definitively open. The small jugs 1 and the cursors 2 shall be packed as dangerous waste at an extremely high cost as the infiltration of the liquid in the center of their walls established with the plastic materials used prevents the decontaminations from being effective.

The cap 4 can sometimes fall off in the pipes and requires dismantlings be made to recover the elements of the system with extremely restrictive precautions so as to maintain containment of the substances.

In practice, analyses are made on several small jugs 1 at the same time. The cursors 2 are marked by a coding but become unusable as soon as the small jugs 1 are extracted from the cursors 2, this operation for separating the small jug 1 from its cursor 2 being dictated by the type and analysis methods used : for example, the measurements for absorbing a radiation or requiring that the contents of the small jug 1 be poured into a tank after opening of the stopper 3. It then becomes impossible to match the small jugs 1 and the corresponding cursors 2 and thus definitely identify the samples, this resulting in a possible risk of confusion of the samples.

The small jug 1, produced by a method for blowing into an external mould, has an internal diameter which varies widely which compromises the accuracy of the measurements, such as the absorption measurements carried out with the aid of a ray which traverses the contents of the small jug 1.

Furthermore, the imperviousness between the small jug 1 and the stopper 3 is not very good and the vacuum, which is firstly established in the small jug 1, gradually ceases.

Finally, the sampling needles frequently pull up the drop catcher 11 from its housing instead of piercing it. The result is that the takings of samples comes to naught.

SUMMARY OF THE INVENTION

The invention concerns a receptacle made up of an open flask intended to contain a substance, a flexible stopper closing the flask by a circular lip moulded onto the opening of the flask and having a pricking surface in front of the opening of the flask, an open casing surrounding the flask and intended to slide into a transport pipe, and an inner capsule closing the casing. This receptacle also has a large number of improved factors.

The most important of these improvements consists in that the stopper is embedded in the inner capsule and the inner capsule is screwed to the casing (and interrupted in front of the pricking surface).

The advantage is that the opening of the flask is carried out in a single operation which lends itself perfectly to automation by remote-controlled unscrewing devices.

Similarly, closing may be easily carried out as many times as desired as the stopper is properly supported by the inner capsule.

Again, it is an advantage that the flask bears a small ring placed on the opening of the casing and secured by welding, gluing or other means to the casing. The flask and the casing then form a single piece and their gap is hermetically closed so that it cannot be polluted.

It is recommended that the inner capsule and either the flask or casing carry a brake for unscrewing the inner capsule so as to avoid a situation similar to pulling up of the cap which would be even more harmful here as the stopper would also be removed. These brakes may consist of a toothed crown on the inner capsule and another toothed crown on the flask-or the casing whose teeth are imbricated with those of the first one.

If in addition the flask is made of plastic obtained by means of moulding, its dimensions may be known accurately and its surface finish is sufficiently satisfactory so that the imperviousness in the vacuum is fully established with the internal lip of the stopper. The drop catcher may be firmly kept in the stopper if the lip comprises an external swelling beyond the drop catcher which provokes a local contraction of the lip so as to reclose it on the ring of the drop catcher as soon as this swelling is engaged in the opening of the flask.

Finally, the oozings of the liquid outside the flask via the pricking surface may be considerably reduced if the pricking surface is thicker than the sloping edge of the needle so as to avoid any communication between the inside and outside of the flask at the time the needle rises or falls.

BRIEF DESCRIPTION OF THE DRAWINGS

There now follows a more detailed illustrative nonrestrictive description of the invention with reference to the accompanying figures:

FIGS. 2a and 2b show details of FIG. 2, and FIG. 3 shows the context for using the receptacle.

DETAILED DESCRIPTION OF THE PREFERRED EMBODIMENTS

Figure 1:
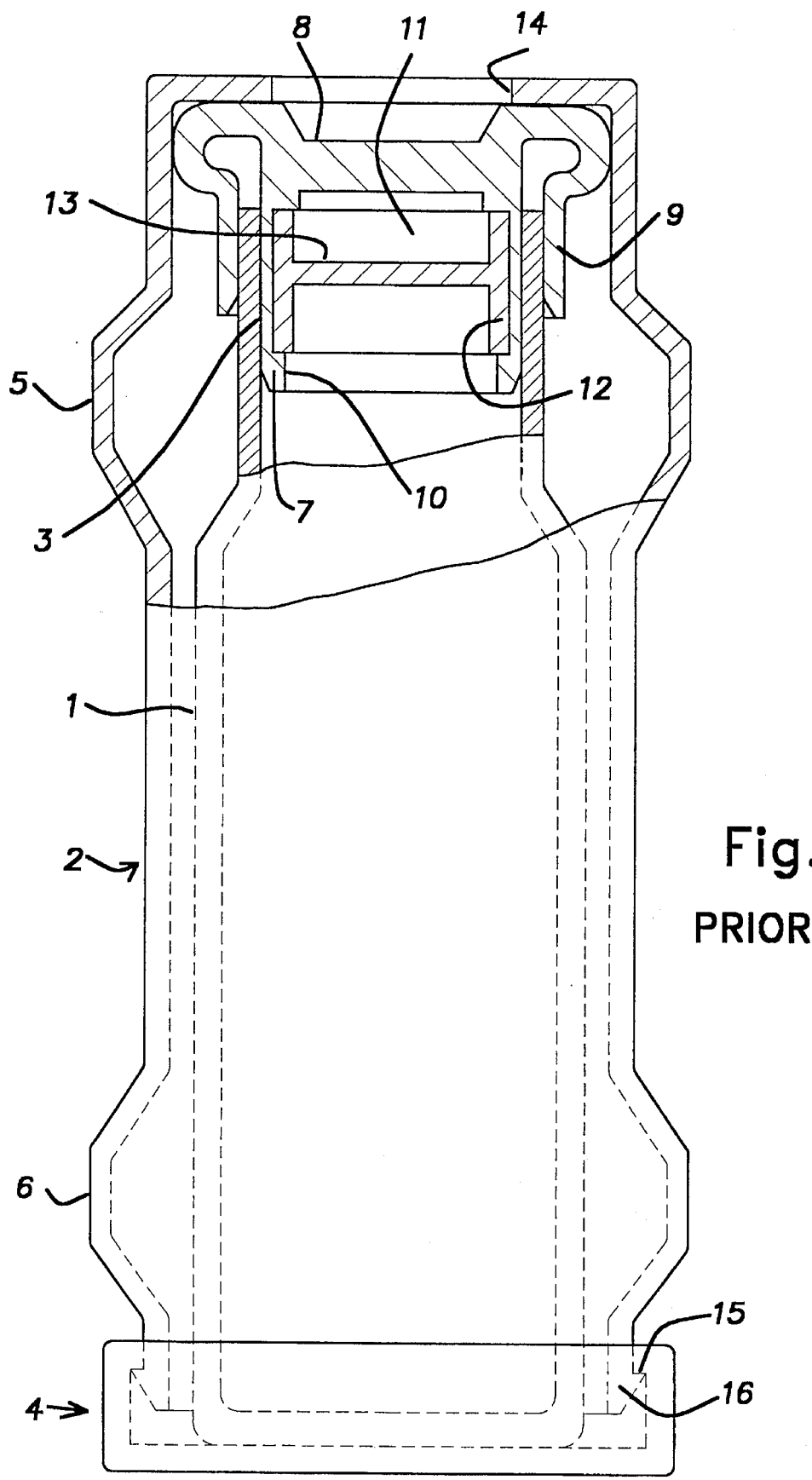
FIG. 1, already described, shows a receptacle of the prior art.
Figure 2:
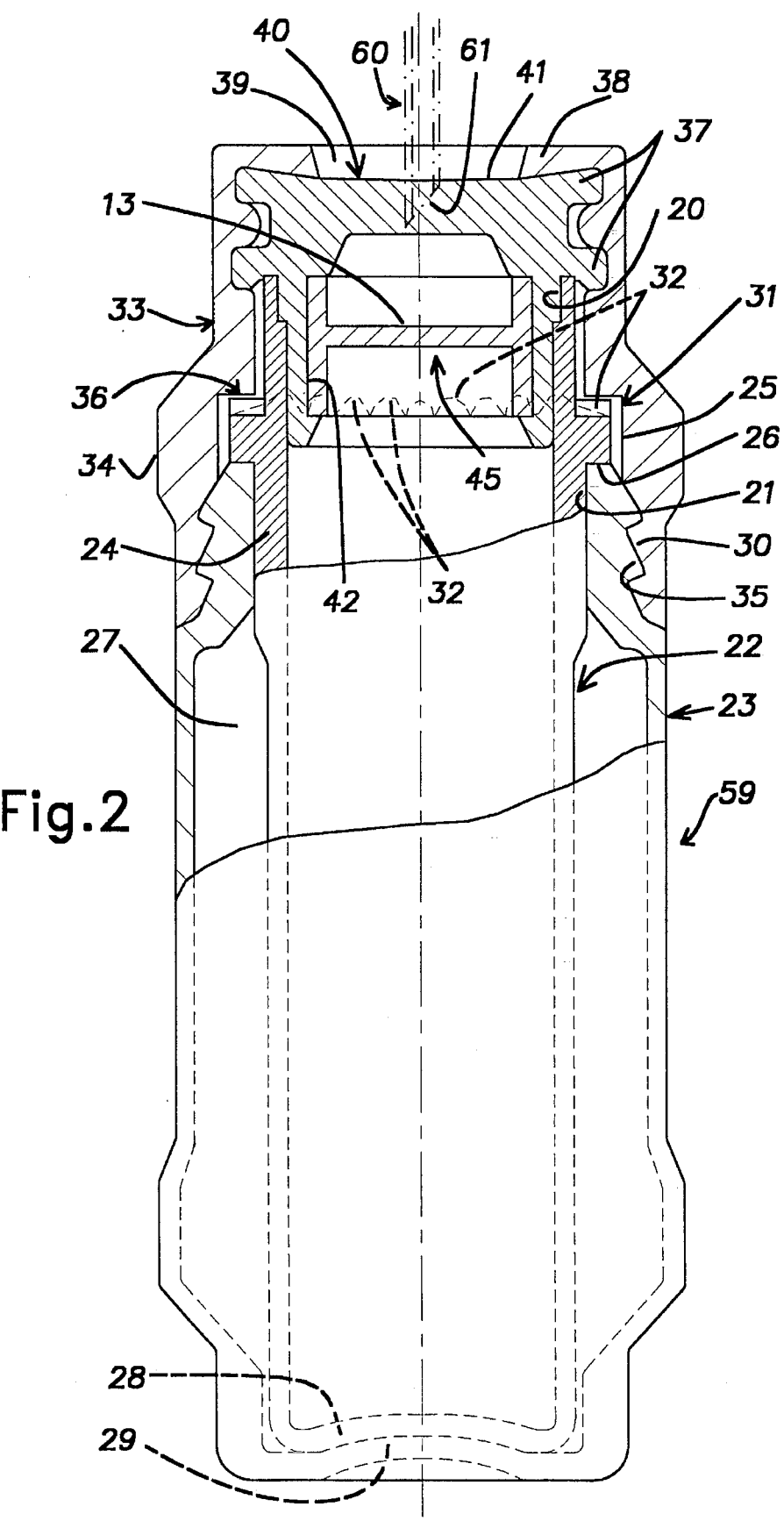
FIG. 2 shows a receptacle conforming to the invention.

With reference to FIG. 2, while the small jug 1 and the cursor 2 of the prior art (FIG. 1) were head-to-head, that is with opposing openings a receptacle 59 according to the present invention has the opening 20 of the small jug or flask 22 and the opening 21 of the cursor or casing 23 are on the same side. The flask 22 is longer than the casing 23 and thus goes past its opening 21 and accurately adjusted to the latter by means of a swollen portion 24 it bears at this location and which projects over its outer surface.

Furthermore, the swollen portion 24 is adjacent to a small ring 25 projecting even further outside the flask 22 and which is placed on a flat bearing surface at the end of the opening 21 of the casing 23. The junction circumference may be glued or welded hermetically sealing the empty volume 27 situated between the flask 22 and the casing 23 which accordingly shall never be polluted. Moreover, the small jug 22 and the casing 23 have nested concave measuring slugs 28 and 29 which offer good centering opposite the openings 20 and 21 and end by rendering integral these two elements.

The opening 21 of the casing 23 bears an external threading 30 and the small ring 25 bears a toothed crown 31 formed of a circumference of teeth 32 having a low-height triangular section which rises up in the direction of the axis common to the flask 22 and the casing 23. This can be clearly seen at the top of FIG. 2a. This can also be established on the top of the casing 23.

Figure 2B:
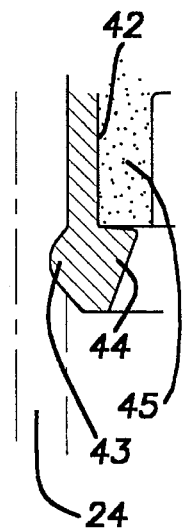

The inner capsule 33 closes the cursor 23 and in particular has a high slightly cylindrical edge 34 bearing an internal screw thread 35 at its lower portion, a toothed crown 36 similar to that 31 of the small jug 22, but these teeth 32 are opposing, and circular striae 37 and a flat end upper surface 38 which is pierced by a hole 39. When the inner capsule 33 is assembled with the rest of the receptacle 59, the internal screw thread 35 is engaged on the threading 30, the teeth 32 of the crowns 31 and 36 are imbricated and oppose any accidental loosening, and the flask 22 is also closed. An elastomer flexible stopper 40 is in fact embedded in the inner capsule 33 and therefore totally integral with it. This is why it is composed of a circular pricking surface 41 whose edge is fitted with small rings compressed in the circular striae 37. The pricking surface 41 mainly extends in front of the hole 39 and is thus visible from the outside. The flexible stopper 40 is composed of an internal lip 42 having a shape similar to that of the prior art but whose outer surface, which is intended to be moulded onto the internal face of the wall of the opening 20, comprises an external swelling 43 projecting towards the outside at the lower end (FIG. 2b) opposite an internal swelling 44 intended as previously to retain a drop catcher 45 which shall not be described again as it is completely similar to that of the prior art. It is assumed that when mounting has been completed, the internal lip 42 is contracted at the end and more firmly retains the drop catcher 45.

The pricking surface 41 is much thicker than in the prior art where it roughly had the same thickness as the valve 13 of the drop catcher 11 (FIG. 1). The pricking surface 41 may be about twice thicker than the valve 13 of the drop catcher 45. When a needle 60 is extracted from the pricking surface 41, its sloping edge 61 in these circumstances has a height smaller than the thickness of the pricking surface 41 and the opening opened up by the needle 60 in this surface then has the possibility of reclosing at any time, either around a continuous portion of the needle 60 above the sloping edge 61, or onto itself when the needle 60 is almost withdrawn, which fully prevents the liquid retained at the end of the needle 60 from oozing outside the pricking surface 41.

Although the skirt 9 (FIG. 1) of the prior art is omitted, the flexible stopper 40 ensures imperviousness of the flask 22 from the oozings of the liquids and the vacuum by virtue of the sole internal lip 42 and even more so if the flask jug 22 is embodied by the injection moulding of plastic around an internal mould as its surface is more regular and smooth. Its dimensions and in particular its internal diameter and thickness are also more regular, accurate and reproducible, which renders the measurements via absorption of radiation through the flask 22 as being more accurate. The portions of the flask 22 and the cursor, apart from the portions of the stopper 40, may be made of other decontaminatable and thus recyclable materials if required, such as stainless steel, TEFLON and glass, although they are more costly and although glass is more fragile, but they cannot be strictly separated.

There are other operations when piercing a receptacle 59 by a needle 60 on FIG. 3 : if required, it is possible to open receptacles 59 or reclose them by having their inner capsule 33 be projected by the claws of an automatic screwing/unscrewing machine 62. This tool, which may be controlled purely automatically, is preferable to using a manual control pair of pliers 64 widely used to date but one which is inconvenient and to be avoided as much as possible.

The contents of the receptacles 59 are transferred by the needle 60 into tanks, such as 65, the contents then being analysed by suitable analysis sensors 66. All these devices, as well as the others which do not form part of the invention as they are already used in the current installation, are disposed in an analysis box 67 out of range of the operators and whose pliers 64 traverse the wall. The receptacles 59 are introduced into the analysis box 67 and are removed from it by pipes 68 in which the receptacles 59 are moved by compressed air injectors 69. The pipes 68 lead to installations for filling the receptacles 59, discharge installations or other analysis boxes.

After these short notations of the technical context of the invention, it shall be observed just how advantageous it is to have receptacles 59 able to be easily handled without there being any risk of false manoeuvre or smears occuring which could be dangerous and which would be clearly difficult to put right by means of remote-handling devices or pliers which only authorize limited actions. The receptacle 59 of the invention and formed of two separable portions instead of five (small jug, stopper, drop catcher, cursor and cap) in the prior art of FIG. 1 authorises a significant simplification of the analysis procedures and enables them to be automated much more easily.

What is claimed is:

1. A receptacle comprising a flask for containing a substance and having an opening, a flexible stopper closing said opening of the flask and having a circular lip moulded onto the opening of the flask and a pricking surface for a needle in front of the opening of the flask, a casing surrounding the flask and having an opening, said casing adapted to slide in a transport pipe, and an inner capsule closing said opening of the casing and screwed to the casing, said inner capsule having an opening in front of the pricking surface of said flexible stopper, wherein said flexible stopper is embedded in said inner capsule.

2. Receptacle according to claim 1, wherein the flask has a small ring engaging a bearing surface surrounding the opening of the casing and fixed to the casing.

3. Receptacle according to claim 1, wherein the inner capsule and one of the flask and the casing have a brake for opposing unwanted unscrewing of the inner capsule from the casing.

4. Receptacle according to claim 3, wherein the brake includes a toothed crown on the inner capsule and another toothed crown on one of the flask and the casing, the toothed crowns being imbricated.

5. Receptacle according to claim 1, wherein the flask comprises moulded plastic.

6. Receptacle according to claim 5, wherein said flask comprises internally moulded plastic such that said opening of said flask has a surface finish sufficient to establish a vacuum seal between said circular lip of said flexible stopper and said opening of said flask.

7. Receptacle according to claim 1, wherein the stopper bears a drop catcher.

8. Receptacle according to claim 7, wherein the circular lip includes an external swelling located near a lower end of the circular lip beyond the drop catcher.

9. Receptacle according to claim 7, wherein the pricking surface is thicker than a length of a sloping edge of the needle for pricking the pricking surface.

10. Receptacle according to claim 1, wherein the flask and the casing have slugs nested inside one another.

* * * * *